(12) United States Patent
Ita

(10) Patent No.: US 6,277,362 B1
(45) Date of Patent: Aug. 21, 2001

(54) AFTER SHAVE TREATMENT PREPARATION

(75) Inventor: Essien Eyo-Okon Ita, South River, NJ (US)

(73) Assignee: ISW, Inc., St. Louis, MO (US)

(*) Notice: Subject to any disclaimer, the term of this patent is extended or adjusted under 35 U.S.C. 154(b) by 0 days.

(21) Appl. No.: 09/427,244

(22) Filed: Oct. 26, 1999

(51) Int. Cl.⁷ .............................. A61K 7/15; A61K 7/48
(52) U.S. Cl. .............................. 424/73; 424/401
(58) Field of Search ....................... 424/73, 401

(56) References Cited

U.S. PATENT DOCUMENTS

| | | |
|---|---|---|
| 4,775,530 | 10/1988 | Perricone . |
| 4,867,967 | 9/1989 | Crutcher . |
| 4,944,939 | 7/1990 | Moore . |
| 5,034,221 | 7/1991 | Rosen et al. . |
| 5,204,093 | 4/1993 | Victor . |
| 5,364,885 | 11/1994 | Ahluwalia et al. . |
| 5,445,823 | 8/1995 | Hall et al. . |
| 5,665,339 | 9/1997 | Simmons . |
| 5,747,021 | 5/1998 | McKenzie et al. . |
| 5,753,244 | 5/1998 | Reynolds et al. . |
| 5,834,513 | 11/1998 | Ptchelintsev et al. . |
| 5,847,003 | 12/1998 | Ptchelintsev et al. . |
| 5,853,709 | 12/1998 | Willis et al. . |
| 5,871,754 | * 2/1999 | Briggs et al. .................. 424/401 |
| 5,885,597 | 3/1999 | Botnecht et al. . |

* cited by examiner

*Primary Examiner*—James M. Spear
(74) *Attorney, Agent, or Firm*—Gibbons, Del Deo, Dolan, Griffinger & Vecchione

(57) ABSTRACT

Non-steroidal anti-infammatory after shave preparations to aid in the prevention and treatment of Pseudofolliculitis Barbae and a method of delivering the ingredients of the preparation to affected areas of the skin. Formula I comprises ethanol, salicylic acid, propylene glycol, glycerine, fragrance, at least one compound for reducing skin irritation and at least one non-steroidal anti-inflammatory agent wherein said non-steroidal anti-inflammatory agent is an NSAID drug, a naturally occurring herbal compound containing an anti-inflammatory component or combinations thereof. Formula 11 comprises water, hydrolyzed oat flour, sorbitol, methylparaben, petrolatum, lanolin, cetyl alcohol, sunflower seed oil, stearic acid, propylparaben, triethanoloamine, a preservative, and at least one non-steroidal anti-inflammatory agent wherein said non-steroidal anti-inflammatory agent is an NSAID drug, a naturally occurring herbal compound containing an anti-inflammatory component or combinations thereof. The formulas have sufficient viscosity to allow the after shave preparation to remain on an affected area of the skin for a sufficient period of time to optimize the skin irritation reduction and anti inflammatory effects on the affected area thus providing local relief from irritation due to PFB.

22 Claims, No Drawings

AFTER SHAVE TREATMENT PREPARATION

FIELD OF THE INVENTION

The present invention relates to an after shave preparation useful in treating the skin disorder known as Pseudofolliculitis Barbae (PFB) sometimes called "razor bumps." This complication can occur on the face and neck area of men and in the bikini area of women as the result of shaving. The after shave treatment reparation is applied to the skin after shaving for treatment and prevention of Pseudofolliculitis Barbae by eliminating or significantly reducing the inflammation and bumps caused by shaving.

BACKGROUND OF THE INVENION

Pseudofolliculitis Barbae or ingrown hairs is a bacterial disorder, usually caused by *staphylococcus aureus*, the characteristic lesions being erythematous papules, and sometimes pustules containing buried hairs. Shaving often induces the condition when hairs which are sharpened by shaving curve back and penetrate the skin proximate the follicle from which the hair initially surfaced, thereby causing the characteristic papules or "razor bumps." The natural curvature of the facial hair of black males makes them particularly susceptible to Pseudofolliculitis Barbae (PFB), especially in the submandibular region of the neck. Many others are also susceptible to the disorder. The bikini area in women, especially, is often affected following shaving.

The prevention of Pseudofolliculitis Barbae has been difficult. One proposed solution is the use of depilatory preparations; however, while this is an effective remedy in achieving removal of hair by non-cutting means before it re-surfaces from the skin, the depilatory itself is an irritant and some hair still may pierce the follicular wall.

U.S. Pat. No. 5,853,709, issued Dec. 29, 1998 to Willis et al. teaches the use of a bacteriostatic/hemo styptic agent in the treatment of Pseudofolliculitis Barbae and U.S. Pat. No. 4,867,967, issued Sep. 19, 1989 to Crutcher discloses the use of povidone iodine in the treatment and prevention of PFB. U.S. Pat. No. 5,204,093, issued Apr. 20, 1993 to Victor teaches the use of benzoyl peroxide in the treatment of PFB.

U.S. Pat. No. 4,775,530 issued Oct. 4, 1998 to Perricone teaches the use of alpha-hydroxy acids in the treatment of Pseudofolliculitis Barbae. U.S. Pat. Nos. 5,847,003 and 5,834,513 disclose novel oxa-acid and di-acids as the "active principals" in the topical treatment of PFB.

U.S. Pat. No. 5,034,221 issued Jul. 23, 1991 to Rosen et al. teaches the use of acetylsalicylic acid, corn starch, isopropyl alcohol and aloe vera in the treatment of Pseudofolliculitis Barbae, while U.S. No. Pat. No. 5,747,021 teaches a similar composition for treatment of PFB further including carbomer and water to eliminate the chalky appearance associated with the use of acetylsalicylic acid.

U.S. Pat. No. 4,944,939 is directed to a steroidal composition in combination with salicylic acid for the treatment and prevention of Pseudofolliculitis Barbae.

U.S. Pat. No. 5,445,823, issued Aug. 29, 1995 to Hall et al. is directed to compositions which may include the use of pantothenic acid derivatives in combination with benzoyl peroxide to reduce the irritation associated with benzoyl peroxide use in skin disorders not related to Pseudofolliculitis Barbae such as acne and sebhorrhea.

U.S. Pat. No. 5,885,597, issued Mar. 23, 1999 to Botnecht teaches a topical steroid in combination with an arylpropionic acid analgesic such as ibuprofen and a p-amino-benzoic acid ester type analgesic for the relief of pain.

U.S. Pat. No. 5,665,339, issued Sep. 9, 1997 to Simmons teaches an anhydrous after shave preparation comprising a silicone fluid in combination with 10–90% alcohol and a perfume which preparation may include anti-inflammatories, salicylic acid, propylene glycol and/or glycerol and pantothenic acid derivatives. This silicone-containing composition is directed to achieving superior skin feel rather than treating Pseudofolliculitis Barbae.

SUMMARY OF THE INVENTION

The present invention comprises a non-steroidal anti-inflammatory after shave preparation to aid in the prevention and treatment of Pseudofolliculitis Barbae and a method of delivering the ingredients of the preparation to the affected areas of the skin. The after shave preparation of the invention is applied twice daily (after shaving or hair removal by other means and again before retiring at night) in order to maximize the beneficial effects of the preparation through an entire twenty-four hour period. Further, the after shave preparation of the invention helps improve the overall condition of the skin.

One object of the invention is to provide an after shave preparation to aid in prevention and treatment of Pseudofolliculitis Barbae said preparation comprising ethanol, salicylic acid, propylene glycol, glycerine, fragrance, at least one compound for reducing skin irritation associated with Pseudofolliculitis Barbae selected from the group consisting of panthenol, pantothenic acid, pantetheine, and pantethine; and at least one non-steroidal anti-inflammatory agent wherein said agent is an NSAID drug, a naturally occurring herbal compound containing an anti-inflammatory component, or a combination thereof.

Another object of the invention is to provide an after shave preparation to aid in prevention and treatment of Pseudofolliculitis Barbae said preparation comprising water, hydrolyzed oat flour, sorbitol, methylparaben, petrolatum, lanolin, cetyl alcohol, sunflower seed oil, stearic acid, propylparaben, triethanoloamine, a preservative, and at least one non-steroidal anti-inflammatory agent wherein said agent is an NSAID drug, a naturally occurring herbal compound containing an anti-inflammatory component or a combination thereof.

A further object of the invention is to provide after shave preparations to aid in the prevention and treatment of Pseudofolliculitis Barbae with sufficient viscosity to allow the preparation to remain on an affected area of the skin for a sufficient period of time to optimize the therapeutic effects on the affected area thus providing local relief from irritation due to PFB.

The foregoing and other objects and advantages of the invention will become apparent from the more detailed description of the invention.

DETAILED DESCRIPTION OF THE INVENTION

The ingredients of the present invention include compounds which reduce the swelling and irritation associated with the "razor bumps" which are characteristic of Pseudofolliculitis Barbae and are effective in preventing recurrence of the disorder.

Anti-irritants useful in the present invention preparations may be selected from the group consisting of panthenol, pantothenic acid, pantetheine, and pantethine.

Also useful are non-steroidal anti-inflammatory drugs (NSAIDS). The NSAIDS can be selected from the following categories: propionic acid derivatives, acetic acid derivatives, biphenylcarboxylic acid derivatives, fenamic acid derivatives and oxicams. All of these NSAIDS are fully described in U.S. Pat. No. 4,985,459 to Sunshine et al. issued Jan. 15, 1991. Most preferred are the propionic NSAIDS including but not limited to acetylsalicylic acid, acetaminophen, ibuprofen, naproxen, benoxaprofen, flurbiprofen, fenoprofen, fenobufen, ketoprofen, indogrofen, pirprofen, caprofen, oxaprozin, pranoprofen, miroprofen, tioxaprofen, suprofen, almionoprofin, tiaprofemic acid, fluprofen and bucloxic acid.

Also useful are naturally occurring herbal compounds containing anti-inflammatory components. Such ingredients may include but are not limited to willow bark, turmeric root, licorice root and ginger root.

The after shave preparations of the present invention result from the combinations of:

Ethanol, glycerine, propylene glycol, salicylic acid, fragrance, at least one compound for reducing skin irritation associated with Pseudofolliculitis Barbae selected from the group consisting of panthenol, pantothenic acid, pantetheine, and pantethine, and, at least one non-steroidal anti-inflammatory agent wherein said agent is an NSAID drug, a naturally occurring herbal compound containing an anti-inflammatory component or a combination thereof (FORMULA I); or Water, hydrolyzed oat flour, sorbitol, methylparaben, petrolatum, lanolin, cetyl alcohol, sunflower seed oil, stearic acid, propylparaben, triethanoloamine, a preservative, preferably allatoin, and at least one non-steroidal anti-inflammatory agent, wherein said agent is an NSAID drug, a naturally occurring herbal compound containing an anti-inflammatory component or combinations thereof (FORMULA II).

It will be understood by the artisan that when selecting an anti-inflammatory agent which is a naturally occurring herbal compound containing an anti-inflammatory component, the weight percent of the selected compound in the after shave preparation will be adjusted according to the relative amount of anti-inflammatory component in the compound.

The preparations have sufficient viscosity such that the preparation remains on the skin for a sufficient length of time to maximize the efficaciousness of the ingredients in combating Pseudofolliculitis Barbae for 24 hours or an entire day.

EXAMPLES

The following examples serve to further describe and demonstrate embodiments within the scope of the invention but are not to be construed as limitations to the present invention as many variations are possible without departing from the spirit of the invention. The scope of the invention is described in the claims which follow.

It has been found that the following after shave preparations are useful in treating Pseudofolliculitis Barbae when kept on the affected area of the skin for an optimal amount of time by keeping the ingredients, preferably, within the following ranges, based on Formula I (Example 1) and Formula II (Example 2) respectively:

Example 1

| | INGREDIENT | WEIGHT PERCENT RANGE |
|---|---|---|
| A) | SALICYLIC ACID | 0.25–17 |
| B) | PROPYLENE GLYCOL | 0.15–15 |
| C) | GLYCERINE | 0.15–15 |
| D) | PANTETHINE | 0.15–18 |
| E) | FRAGRANCE | 0.01–8 |
| F) | IBUPROFEN | 1–35 |
| G) | ETHANOL | Balance to 100% |

The preparation of the above example, which is based on FORMULA I, contains pantethine as an anti-irritant compound and the NSAID selected is ibuprofen. The compound is prepared by first weighing all of the ingredients separately. Ethanol, glycerine and propylene glycol are added to the mixing container of a high-speed mixer with vigorous mixing at ambient temperature to form a mixture. Pantethine, salicylic acid, fragrance and ibuprofen are then slowly added to the mixture with vigorous stirring. When all of the ingredients have been introduced into the mixture, it is mixed for an additional 1 to 3 minutes at moderate to high speed.

Example 2

| | INGREDIENT | WEIGHT PERCENT RANGE |
|---|---|---|
| A) | WATER (for Step 1 below) | 2–30 |
| B) | HYDROLYZED OAT FLOUR | 0.5–10 |
| C) | WATER (for Step 2 below) | 1.0–80 |
| D) | SORBITOL | 1–5 |
| E) | METHYLPARABEN | 0.1–4 |
| F) | PETROLATUM | 1–6 |
| G) | LANOLIN | 1–6 |
| H) | CETYL ALCOHOL | 1–5 |
| I) | SUNFLOWER SEED OIL | 1–30 |
| J) | STEARIC ACID | 0.1–5 |
| K) | PROPYLPARABEN | 0.1–5 |
| L) | TRIETHANOLAMINE | 0.1–5 |
| M) | ALLATOIN | 0.1–5 |
| N) | NAPROXEN | 1.0–35 |

The preparation of the above example, which is based on FORMULA II, contains naproxen as the selected NSAID and is prepared as follows:

Step 1. Hydrolyzed oat flour is added to hot water (about 750° C. to about 100° C.) and the mixture blended in a blender at high speed for about 2.5 minutes and set aside;

Step 2. In a separate container water, sorbitol and methylparaben are heated to about 75° C. to form a mixture;

Step 3. In another separate container petrolatum, lanolin, cetyl alcohol, sunflower seed oil, stearic acid and propylparaben are heated to about 75° C. and stirred to form a mixture;

Step 4. The mixtures of Step 2 and Step 3 are combined with agitation and triethanolamine is added, maintaining heat at about 750 C and agitation for about 10 minutes to form a mixture.

Step 5. After agitation in step 4 is complete, the hydrolyzed oat flour mixture of Step 1 is added to the mixture of step 4 and stirred while cooling.

Step 6. When the temperature reaches 450 C, the allatoin (or any other suitable preservative) and the naproxen are added and mixing is continued until the mixture is homogeneous.

Step 7. The preparation is allowed to cool to ambient temperature.

The preparations of Examples 1 and 2 are characterized by exhibiting a viscosity from about 150 cps to about 50,000 cps at about 22° C. as measured by a Brookfield viscometer at 10 rpm and the number 5 spindle. This viscosity level allows the efficacious ingredients to remain on the skin for an optimal period of time.

The preferred ranges of the ingredients in both formulations remain on the face for 24 hours, effectively fighting PFB when applied to the affected area immediately after shaving and not rinsed off until retiring for bed (at which time another application is applied).

While not being bound to any particular theory as to how ingredients in both formulas work, it is believed that the ingredients function as hereafter described.

In preparations based on Formula 1, the ethanol acts as a carrier for the fragrance and a solvent for the anti-inflammatory agent. The combination of propylene glycol and glycerine not only provides lubricity or slip, but acts as a moisture barrier and humectant between the skin and environment. This allows the therapeutic ingredients to perform to their maximum capabilities to fight PFB. The salicylic acid and pantethine combination forms a unique anti-bacterial and skin replenishing component, while the ibuprofen (or other ethanol soluble NSAID or herbal anti-inflammatory) acts as an anti-inflammatory agent to reduce or eliminate "razor bumps" thus allowing shaved hair to grow out of the hair follicle without obstruction.

In preparations based on Formula 11, water provides moisture to the skin and dissolves the other water soluble ingredients in the formula. Hydrolyzed oat flour provides natural moisture to the skin and, since it has natural therapeutic/healing properties, it also soothes and heals the affected area. Sorbitol acts as a humectant and moisture barrier that allows the therapeutic ingredients to remain on the skin. Methyl and propylparaben are preservatives. Petrolatum, lanolin, cetyl alcohol, sunflower seed oil and stearic acid act as emollients and emulsifiers. The anti-inflammatory naproxen (or other fat or water soluble NSAID or herbal anti-inflammatory) acts as the "razor bump" eliminator or reducer.

Both formulas (I and II) may be used by observing the following directions:

1 Shave (depilatory, razor blade, clippers, or electric razor) using any preferred method.

2) Apply a coat of a present invention after shave preparation to the shaven area and let dry.

3) At night, before going to bed, wash the shaven area and let dry. Re-apply a coat of the present invention preparation to the shaven area.

It has been found that an individual can skip several days of shaving without experiencing PFB as long as the after shave preparation of the present invention is applied twice a day as in the above procedure.

While the invention has been described with reference to the preferred embodiments, it should be appreciated that the invention may embody other percentages of the ingredients than those specifically shown and described and still be effective for treating the skin disorder Pseudofolliculitis Barbae. Accordingly, changes or modifications can be made in the after shave treatment preparation formulation without departing from the principles of the invention, which are defined in the appended claims.

What is claimed is:

1. An after shave preparation to aid in treatment of Pseudofolliculitis Barbae comprising:
    (a) propylene glycol;
    (b) glycerine;
    (c) ethanol;
    (d) salicylic acid;
    (e) a compound for reducing skin irritation associated with Pseudofolliculitis Barbae selected from the group consisting of panthenol, pantothenic acid, pantetheine, pantethine and mixtures thereof; and,
    (f) at least one non-steroidal anti-inflammatory agent in an amount effective to reduce inflammation caused by Pseudofolliculitis Barbae
    wherein said non-steroidal anti-inflammatory agent is a naturally occurring herbal compound containing an anti-inflammatory component.

2. The after shave preparation of claim 1 further comprising
    (g) fragrance.

3. A method for treating Pseudofolliculitis Barbae comprising applying to an affected area of skin an effective amount to provide local relief from irritation due to Pseudofolliculitis Barbae of an after shave preparation, said preparation comprising
    (a) Propylene glycol;
    (b) glycerine;
    (c) ethanol;
    (d) salicylic acid;
    (e) a compound for reducing skin irritation associated with Pseudofolliculitis Barbae selected from the group consisting of panthenol, pantothenic acid, pantetheine, pantethine and mixtures thereof; and,
    (f) at least one non-steroidal anti-inflammatory agent in an amount effective to reduce inflammation caused by Pseudofolliculitis Barbae
    wherein said non-steroidal anti-inflammatory agent is an NSAID drug, a naturally occurring herbal compound containing an anti-inflammatory component or combinations thereof.

4. The after shave preparation of claim 1 wherein said compound for reducing skin irritation is pantethine.

5. The after shave preparation of claim 4 wherein weight percent ranges are as follows:

| | INGREDIENT | WEIGHT PERCENT RANGE |
|---|---|---|
| A) | SALICYLIC ACID | 0.25–1 7 |
| B) | PROPYLENE GLYCOL | 0.15–15 |
| C) | GLYCERINE | 0.15–15 |
| D) | PANTETHINE | 0.15–18 |
| E) | FRAGRANCE | 0.01–8 |
| F) | [IBUPROFEN] herbal anti-inflammatory agent | 1–35 |
| G) | ETHANOL | Balance to 100% |

6. The after shave preparation of claim 1 wherein said preparation has a viscosity from about 150 to about 50,000 cps.

7. The method of claim 3 wherein said after shave preparation further comprises
    (g) fragrance.

8. The method of claim 3 wherein said non-steroidal anti-inflammatory agent is ibuprofen.

9. An after shave preparation to aid in treatment of Pseudofolliculitis Barbae or ingrown hairs comprising water, hydrolyzed oat flour, sorbitol, petrolatum, lanolin, cetyl alcohol, sunflower seed oil, stearic acid, triethanolamine, and at least one non-steroidal anti-inflammatory agent wherein said non-steroidal anti-inflammatory agent is an NSAID drug, a naturally occurring herbal compound containing an anti-inflammatory component or combinations thereof.

10. The after shave preparation of claim 9 further including a preservative.

11. The after shave preparation of claim 10 wherein said preservative is selected from the group consisting of methylparaben, propylparaben, allatoin and combinations thereof.

12. The after shave preparation of claim 9 wherein said non- steroidal anti-inflammatory agent is naproxen.

13. The after shave preparation of claim 11 wherein said non- steroidal anti-inflammatory agent is naproxen.

14. The after shave preparation of claim 13 wherein said compound for reducing skin irritation is pantethine.

15. The after shave preparation of claim 14 wherein weight percent ranges as follows:

|    | INGREDIENT          | WEIGHT PERCENT RANGE |
|----|---------------------|----------------------|
| A) | WATER               | 12–93                |
| B) | HYDROLYZED OAT FLOUR| 0.5–10               |
| D) | SORBITOL            | 1–5                  |
| E) | METHYLPARABEN       | 0.1–4                |
| F) | PETROLATUM          | 1–6                  |
| G) | LANOLIN             | 1–6                  |
| H) | CETYL ALCOHOL       | 1–5                  |
| I) | SUNFLOWER SEED OIL  | 1–30                 |
| J) | STEARIC ACID        | 0.1–5                |
| K) | PROPYLPARABEN       | 0.1–5                |
| L) | TRIETHANOLAMINE     | 0.1–5                |
| M) | ALLATOIN            | 0.1–5                |
| N) | NAPROXEN            | 1.0–35               |

16. The after shave preparation of claim 9 wherein said preparation has a viscosity from about 150 cps to about 50,000 cps.

17. The after shave preparation of claim 15 wherein said preparation has a viscosity from about 150 cps to about 50,000 cps.

18. A method for treating Pseudofolliculitis Barbae comprising applying to an affected area of skin an effective amount of the preparation of claim 9 to provide local relief from irritation due to Pseudofolliculitis Barbae.

19. A method for treating Pseudofolliculitis Barbae comprising applying to an affected area of skin an effective amount of the preparation of claim 15 to provide local relief from irritation due to Pseudofolliculitis Barbae.

20. The method of claim 8 wherein said compound for reducing skin irritation is pantethine.

21. The method of claim 20 wherein weight percent ranges in said after shave preparation are as follows:

|    | INGREDIENT       | WEIGHT PERCENT RANGE |
|----|------------------|----------------------|
| A) | SALICYLIC ACID   | 0.25–17              |
| B) | PROPYLENE GLYCOL | 0.15–15              |
| C) | GLYCERINE        | 0.15–15              |
| D) | PANTETHINE       | 0.15–18              |
| E) | FRAGRANCE        | 0.01–8               |
| F) | IBUPROFEN        | 1–35                 |
| G) | ETHANOL          | Balance to 100%      |

22. The method of claim T wherein said after shave preparation has a viscosity from about 150 to about 50,000 cps.

* * * * *

UNITED STATES PATENT AND TRADEMARK OFFICE
CERTIFICATE OF CORRECTION

PATENT NO.    : 6,277,362 B1
DATED         : August 21, 2001
INVENTOR(S)   : Essien Eyo-Okon Ita It is certified that error appears in the above-identified patent and that said Letters Patent is hereby corrected as shown below:

<u>Column 4,</u>
Line 49, please change "750ºC" to read -- 75ºC --;
Line 59, please change "750ºC" to read -- 75ºC --; and
Line 64, please change "450ºC" to read -- 45ºC --.

Signed and Sealed this

Eleventh Day of March, 2003

JAMES E. ROGAN
*Director of the United States Patent and Trademark Office*